US009914975B2

(12) United States Patent
Meldgaard et al.

(10) Patent No.: US 9,914,975 B2
(45) Date of Patent: Mar. 13, 2018

(54) EGFR BLOOD MONITORING

(71) Applicant: Roche Molecular Systems, Inc., Pleasanton, CA (US)

(72) Inventors: Peter Meldgaard, Abyhoj (DK); Boe Sorensen, Beder (DK); Julie Tsai, Newark, CA (US); Wei Wen, Santa Clara, CA (US); Lin Wu, Moraga, CA (US)

(73) Assignees: Roche Molecular Systems, Inc., Pleasanton, CA (US); Aarhus University, Viborg (DK)

( * ) Notice: Subject to any disclaimer, the term of this patent is extended or adjusted under 35 U.S.C. 154(b) by 0 days.

(21) Appl. No.: 15/098,150

(22) Filed: Apr. 13, 2016

(65) Prior Publication Data

US 2016/0237507 A1    Aug. 18, 2016

Related U.S. Application Data

(62) Division of application No. 14/200,744, filed on Mar. 7, 2014, now abandoned.

(60) Provisional application No. 61/774,946, filed on Mar. 8, 2013.

(51) Int. Cl.
   *C12Q 1/68* (2006.01)
   *A61K 31/517* (2006.01)
   *A61K 31/5377* (2006.01)

(52) U.S. Cl.
   CPC .......... *C12Q 1/6886* (2013.01); *A61K 31/517* (2013.01); *A61K 31/5377* (2013.01); *C12Q 2600/106* (2013.01); *C12Q 2600/156* (2013.01)

(58) Field of Classification Search
   CPC ............ C12Q 1/6886; C12Q 2600/156; C12Q 2600/106; A61K 31/517; A61K 31/5377
   See application file for complete search history.

(56) References Cited

U.S. PATENT DOCUMENTS

| | | | |
|---|---|---|---|
| 5,210,015 | A | 5/1993 | Watson et al. |
| 5,804,375 | A | 9/1998 | Watson et al. |
| 5,972,602 | A | 10/1999 | Hyland et al. |
| 6,033,854 | A | 3/2000 | Chiang et al. |
| 6,127,155 | A | 10/2000 | Gelfand et al. |
| 6,180,349 | B1 | 1/2001 | Jensen et al. |
| 6,521,409 | B1 | 2/2003 | Benko et al. |
| 7,442,507 | B2 | 10/2008 | Chapman et al. |
| 7,960,118 | B2 | 6/2011 | Seshagiri |
| 7,964,349 | B2 | 6/2011 | Paez et al. |
| 8,067,175 | B2 | 11/2011 | Pao et al. |
| 2007/0020648 | A1 | 1/2007 | Liu et al. |
| 2010/0041048 | A1 | 2/2010 | Diaz et al. |
| 2014/0272953 | A1 | 9/2014 | Klughammer et al. |

FOREIGN PATENT DOCUMENTS

| | | |
|---|---|---|
| WO | 2002/088388 A1 | 11/2002 |
| WO | 2012/085229 A1 | 6/2012 |
| WO | 2014/135669 A1 | 9/2014 |

OTHER PUBLICATIONS

Dias et al., Non-small cell lung cancer: Are M1a and M1b the same stage? European Respiratory Journal 46: PA4288, 2015.*
U.S. Appl. No. 14/200,522, "Non-Final Office Action", dated Aug. 7, 2015, 28 pages.
U.S. Appl. No. 14/200,522, "Restriction Requirement", dated Apr. 14, 2015, 6 pages.
Didelot, et al., "Competitive allele specific TaqMan PCR for KRAS, BRAF and EGFR mutation detection in clinical formalin fixed paraffin embedded samples", Experimental and Molecular Pathology, vol. 92, No. 3, Jun. 2012, pp. 275-280.
The International Search Report and Written Opinion from International Application No. PCT/EP2014/054409, dated Jun. 27, 2014.
The Written Opinion from International Application No. PCT/EP2014/054409, dated Feb. 11, 2015.
Bai et al., "Epidermal Growth Factor Receptor Mutations in Plasma DNA Samples Predict Tumor Response in Chinese Patients With Stages IIIB to IV Non-Small-Cell Lung Cancer," *J. Clin. Oncol.*, 2009, 27(16):2653-2659.
Brevet et al., "Detection of EGFR mutations in plasma DNA from lung cancer patients by mass spectrometry genotyping is predictive of tumor EGFR status and response to EGFR inhibitors," *Lung Cancer* 2010, 73(1):96-102.
DeGraves et al., "High-sensitivity quantitative PCR platform," *Biotechniques*, 2003, 34(1):106-115.
Deiman et al., "Characteristics and applications of nucleic acid sequence-based amplification (NASBA)," Mol. Biotechnol., 2002, 20(2):163-179.
Gibson et al., "A novel method for real time quantitative RT-PCR," *Genome Res.*, 1996, 6(10):995-1001.
He et al., "Detection of epidermal growth factor receptor mutations in plasma by mutant-enriched PCR assay for prediction of the response to gefitinib in patients with non-small-cell lung cancer," 2009, *Int. J. Cancer*, 125:2393-2399.
Heid et al., "Real Time Quantitative PCR," *Genome Res.*, 1996, 6(10):986-994.
Holland et al., "Detection of specific polymerase chain reaction product by utilizing the 5'→3' exonuclease activity of Thermus aquaticus DNA polymerase," *Proc. Natl. Acad. Sci. USA*, 1991, 88(16):7276-7280.
Karachaliou et al., "Association of EGFR L858R Mutation in Circulating Free DNA With Survival in the EURTAC Trial," 2015, *JAMA Oncol.*, pp. E1-E9. Published online Feb. 26, 2015 at doi:10.1001/jamaoncol.2014.257.
Kopreski et al., "Somatic Mutation Screening: Identification of Individuals Harboring K-ras Mutations With the Use of Plasma DNA," 2000, *J. Natl. Cancer Inst.*, 92:918-923.
Kuang et al., "Noninvasive Detection of EGFR T790M in Gefitinib or Erlotinib Resistant Non-Small Cell Lung Cancer," *Clin. Cancer Res.*, 2009, 15(8):2630-2636.
Lynch et al., "Activating Mutations in the Epidermal Growth Factor Receptor Underlying Responsiveness of Non-Small-Cell Lung Cancer to Gefitinib," *N. Engl. J. Med.*, 2004, 350:2129-2139.

(Continued)

*Primary Examiner* — Ruixiang Li
(74) *Attorney, Agent, or Firm* — Carol Johns

(57) ABSTRACT

Improved methods of assessing status of a solid-tumor cancer in a subject involving detection of tumor-associated mutations in the subject's blood.

9 Claims, 8 Drawing Sheets

(56) References Cited

OTHER PUBLICATIONS

Nygaard et al., "The correlation between cell-free DNA and tumour burden was estimated by PET/CT in patients with advanced NSCLC," 2014, *Br. J. Cancer*, 110:363-368.

Paez et al., "EGFR Mutations in Lung Cancer: Correlation with Clinical Response to Gefitinib Therapy," *Science*, 2004, 304:1497-1500.

Pao et al., "Epidermal Growth Factor Receptor Mutations, Small-Molecule Kinase Inhibitors, and Non-Small-Cell Lung Cancer: Current Knowledge and Future Directions," 2005, *J. Clin. Oncol.*, 23:2556-2568.

Qin et al., "Comparison of three methods for detecting epidermal growth factor receptor mutations in plasma DNA samples of Chinese patients with advanced non-small cell lung cancer," *Chinese Medical Journal*, 2011, 124(6):887-891.

Rosell et al., "Epidermal Growth Factor ReceptorActivation: How Exon 19 and 21 Mutations Changed Our Understanding of the Pathway," *Clin. Cancer Res.*, 2006, 12(24):7222-7231.

Ryan et al., "A prospective study of circulating mutant KRAS2 in the serum of patients with colorectal neoplasia: strong prognostic indicator in postoperative follow up," 2003, *J. Clin. Pathol. Mol Pathol.*, 56:172-179.

Sharma et al., "Epidermal growth factor receptor mutations in lung cancer," *Nat. Rev. Cancer*, 2007, 7(3):169-181.

qPCR Somatic Mutation PCR Handbook, Aug. 2012.

\* cited by examiner

EGFR BLOOD MONITORING

PRIOR RELATED APPLICATIONS

The present application claims the benefit of U.S. Provisional Patent Application No. 61/774,946, filed Mar. 8, 2013, and U.S. patent application Ser. No. 14/200,744, filed Mar. 7, 2014, the disclosures of which are hereby incorporated by reference in their entireties.

BACKGROUND OF THE INVENTION

Germline and somatic mutations affecting various cell proliferation pathways are known to affect the development of cancer in patients. For example, the acquisition of somatic mutations that confer growth advantage on the cells possessing such mutations is considered an important factor in the emergence and progression of cancerous tumors. As a number of such mutations was identified, the therapies were developed that target the proteins encoded by the mutated genes, as well as the therapies targeting the signaling pathways in which these mutated genes are involved. As these targeted therapies were implemented into clinical practice, it was discovered that mutations conferring the resistance to the targeted therapies develop and accumulate in the patients' cancerous tumors, over time rendering the therapy ineffective and making it necessary to change the course of treatment.

One example of a solid tumor cancer in which somatic tumor mutations are known to play an important role is lung cancer, which is a leading cause of cancer-related mortality in many countries, including the United States. Approximately 75% of lung cancer cases belong to non-small cell lung cancer (NSCLC), which has an overall 5-year survival rate of approximately 12%. Standard surgical treatment, as well as chemotherapy and radiotherapies are available in the field of NSCLC. However, the majority of the NSCLC cases are initially diagnosed at the inoperable late stage, and relapse is common following surgery, chemotherapy, radiotherapy and other treatments. Accordingly, treatment and diagnosis of NSCLC is a challenging medical problem. One attempt at addressing the problem was the development of the targeted drug therapies that interfere with the signaling of epidermal growth factor receptor (EGFR). EGFR, which is a member of the growth factor receptor family of tyrosine kinases, is involved in signaling pathways related to cell division and is implicated in NSCLC development and progression.

Small molecule drugs erlotinib and gefitinib, which inhibit tyrosine kinase activity of EGFR, were evaluated and approved for treatment of late stage NSCLC. It was discovered, however, that these drugs were net effective in the majority of NSCLC patients, but are most effective in a subset of patients whose tumors contain somatic EGFR mutations that lead to an increase in the tyrosine kinase activity of EGFR. This type of mutations is often termed "activating." Somatic EGFR mutations that lead to resistance to tyrosine kinase inhibitor therapy in NSCLC patients were also discovered. This type of mutations is often termed "resistance." Resistance mutations in EGFR tend to arise in NSCLC patients during the course of tyrosine kinase inhibitor treatment. In the cases of NSCLC that cannot be effectively treated by tyrosine kinase inhibitor therapy, such as erlotinib and gefitinib, chemotherapy remains the most effective treatment to prolong survival. To improve the chances of selecting an effective treatment for NSCLC patients, it is therefore important to determine whether the patients' NSCLC tumors contain somatic EGFR mutations that confer sensitivity or resistance to tyrosine kinase inhibitor therapy.

The above example of the role of EGFR somatic mutations in the development of NSCLC illustrates how detecting the presence or emergence of certain mutations in the cancerous tumors is generally important for choosing an effective cancer treatment. For example, detecting the presence or emergence of somatic mutations leading to targeted drug therapy resistance in cancer patients is essential for monitoring the therapy and assessing disease progression. Therefore, it is generally beneficial to develop convenient and reliable methods of testing for somatic mutations in the tumors of the cancer patients in order to improve cancer assessment, including, but not limited to, diagnostics, monitoring, and treatment selection in such patients.

One way of detecting such mutations is testing tumor samples obtained through biopsy or surgery for the presence of mutant sequences associated with cancer development. However, tumor tissue samples may not be immediately available for testing. To avoid delay in detection of the cancer-associated mutations and selection of appropriate treatment as well as to spare the patients from invasive procedures, it is beneficial to develop more expedient and less invasive methods for detecting mutations in the tumors of the cancer patients.

It is known that tumor cells circulate in the blood of patients with solid tumor cancers, thus making it possible to detect somatic tumor mutations in the blood samples of cancer patients, including detection of EGFR mutations in NSCLC patients. However, it is difficult to reliably adapt such detection for meaningful clinical and diagnostic use due to the small amount of circulating mutated sequences, background of non-mutated sequences and high levels of genomic DNA (gDNA) circulating in the blood, the gDNA originating from broken white blood cells (WBC). Detection of mutated nucleic acid sequences originating from tumor cells in blood samples, such as detection of EGFR mutations in NSCLC patients, suffers from inaccuracies, such as relatively high false negative detection rates, and often requires cumbersome analytical techniques that may involve, for example, isolation of blood-circulating tumor cells prior to detection, or enrichment of the content of mutated DNA sequences in the sample prior to detection. Quantitative detection can be even more difficult, due to high background DNA levels, among other things. It is therefore important to develop improved methods of detection of mutated tumor nucleic acid sequences in the blood of cancer patients, such as detection of mutated EGFR nucleic acid sequences in the blood of NSCLC patients, to make such detection methods useful for assessment of cancer in clinical and diagnostic practice.

BRIEF SUMMARY OF THE INVENTION

Described herein are improved methods of assessing status of a subject with a solid tumor cancer, comprising detecting presence or absence of one or more tumor nucleic acid mutations in a blood of the subject with the solid tumor cancer; and, assessing the status of the subject with the solid tumor cancer based on the detected presence or absence of the one or more tumor nucleic acid mutations. The improved methods may involve detection of the one or more tumor nucleic acid mutations by performing a quantitative real-time polymerase chain reaction (PCR) on a blood sample or on a total genomic DNA isolated from a blood sample, where the blood sample is obtained from a subject with a solid tumor cancer. Also described herein are improved methods of detecting presence or absence of an tumor mutation in a blood sample obtained from a subject with a solid tumor cancer, comprising performing a quantitative real-time polymerase chain reaction (PCR) on the blood sample using primers specific for a mutated nucleic sequence to generate a PCR cycle threshold. In some embodiments of the improved methods described herein, a metastatic status of the subjects' with a solid tumor cancer is taken into account in order to improve sensitivity of the detection of the mutated tumor nucleic acid sequences in the blood samples obtained from the subjects. In some other embodiments, detection of the presence or the absence of the one or more tumor nucleic acid mutations in the blood samples obtained from the subjects with the solid tumor cancers involves determining the amount of the mutated sequences circulating in the blood and monitoring the status of the subject's cancer based on the detected amount.

Described herein are methods of assessing status of a subject with distant metastasis NSCLC, comprising: detecting presence or absence of one or more mutated EGFR nucleic acid sequence in blood from the subject with distant metastasis stage NSCLC; and assessing the status of the subject with distant metastasis stage NSCLC based on the detected presence or absence of the one or more mutated EGFR nucleic acid sequence. Also described herein are methods of assessing status of a subject with NSCLC, comprising: detecting presence or absence of one or more mutated EGFR nucleic acid sequence in a blood of the subject; and assessing the status of the subject based on the detected presence or absence of the one or more mutated EGFR sequence. Also described herein are method of identifying a candidate NSCLC patient for a targeted drug therapy, comprising: detecting presence or absence of one or more mutated EGFR sequence in blood from the patient; assessing metastatic status of the NSCLC patient as M1a or M1b; and identifying the patient as a candidate for the targeted drug therapy based on at least the detected presence of the one or more mutated EGFR sequence in the blood of the patient, and the metastatic status of NSCLC in the patient. Also disclosed herein are methods of assessing status of a subject with a solid tumor cancer, comprising: detecting presence or absence of one or more tumor-associated mutated nucleic acid sequence in blood from the subject with the solid tumor cancer; and assessing the status of the subject with distant metastasis solid tumor cancer based on the detected presence or absence of the one or more mutated tumor-associated nucleic acid sequence. Furthermore, disclosed herein are methods of detecting presence or absence of a tumor-associated mutation in a blood sample, the methods comprising: performing a quantitative real-time polymerase chain reaction (PCR) on the blood sample using primers specific for a mutated nucleic sequence to generate a PCR cycle threshold; and comparing the cycle threshold to a control value, wherein the control value takes into account the concentration of genomic DNA in the sample, and wherein if the cycle threshold is below the control value the tumor-associated mutation is present in the sample and if the cycle threshold is above the control value the tumor-associated mutation is absent from the sample. Methods of treating patients or subjects with solid tumor cancers, such as NSCLC, are also envisioned and included within the scope of the methods described herein. Variations and combinations of the above methods and their various steps and substeps are also envisioned and included within the scope of the described methods.

Definitions

The term "subject" as used herein typically refers to a person (human) having a solid tumor cancer, such as NSCLC. It is to be understood, that a subject having a solid tumor cancer can be a patient with a known cancer, meaning the cancer that was detected prior to the performance of the embodiments of the methods of the present invention. A cancer patient can be a relapse cancer patient. For example, a subject having NSCLC can be a patient in whom NSCLC was detected prior to the performance of the embodiments of the methods of the present invention. The NSCLC patient can be a relapse patient.

The terms "recurrent," "recurrence," "relapsed/" "relapse" and related terms are used to refer to cancer that returns after treatment, and to the patients that experience the return of the cancer.

The term "solid tumor cancer" is used herein to denote the cancers that are characterized by the formation of cancerous tumors, or cohesive masses of abnormally proliferating cells, in tissues and organs. It is to be understood that some tumors formed by the solid tumor cancers can be cysts, meaning fluid-filled sacks of tissue. The term "solid tumor cancer" is used herein to distinguish tumor-forming cancers from the so-called blood cancers or hematological malignancies that are formed from hematopoietic (blood-forming) cells and affect blood, bone marrow, and lymph nodes. Examples of solid tumor cancers are carcinomas, or cancers derived from epithelial cells, sarcomas, or cancers arising from connective tissue, germ cell tumors, such as seminomas and dysgerminomas, blastomas, or cancers that derive from precursor cells or embryonic tissue. Some non-limiting examples of solid tumor cancers are lung cancer, breast cancer, colorectal cancer, prostate cancer, thyroid cancer, brain cancer, such as glioblastoma, and bladder cancer. Examples of hematological malignancies are lymphomas, leukemias, myelomas, myelodysplastic syndromes and myeloproliferative diseases.

The term "therapy" is used herein synonymously with the term "treatment." The term "cancer therapy" as used herein encompasses various types of cancer therapy or treatment, including surgery, radiotherapy, chemotherapy, and targeted drug therapy.

"Targeted therapy" or "targeted drug therapy" refer to drug therapy that interferes with the growth of cancer cells by interfering with specific molecules needed for carcinogenesis and tumor growth, rather than by simply interfering with all rapidly dividing cells, as chemotherapy does. An example of targeted drug therapy is tyrosine kinase inhibitor therapy, which uses reversible tyrosine kinase inhibitors to inhibit the activity of tyrosine kinases promoting cell proliferation in certain types of cancers. For example, erlotinib or gefitinib target tyrosine kinase activity of EGFR and are used as a targeted therapy for non-small cell lung cancer.

The term "targeted drag therapy," as used herein, is not limited to the above therapies, but can encompass any drug therapy interfering with a specific target, such as therapies that interfere with EGFR signaling. Targeted drug therapies include, but are not limited to, reversible tyrosine kinase inhibitor therapy, irreversible tyrosine kinase inhibitor therapy, antibody therapy, or any form of small molecule, large molecule or nucleic-acid based therapy, such as gene therapy or small interfering RNA therapy.

The term "tumor-associated mutation" is used herein to denote mutations in nucleic acid sequences that affect development of a solid tumor cancer in a subject. For example, a tumor-associated mutation can activate cellular proliferation, thus leading to emergence of a malignant tumor or escalation of tumor growth. A tumor-associated mutation can confer properties on a tumor that facilitate its spread throughout the subject's body, known as metastasis. A tumor-associated mutation can also be associated with susceptibility or resistance of a cancer to cancer therapies. The term "tumor-associated" can be used in reference to nucleic acids or nucleic acid sequences comprising one or more tumor-associated mutations, such as in an expression "tumor-associated mutated nucleic acid sequence."

The terms "assess," "assessment," "assessing" and the related terms are used herein in reference to cancer, status of cancer or status of a subject with cancer, and in some other contexts. These terms can denote but are not limited to inferring the presence or the absence of cancer-associated mutations in cancerous tumors based on the detected presence or absence of mutated nucleic acid sequences in the subject's blood. The terms "assess," "assessment," "assessing" and the related terms may also encompass, depending on the context, recommending or performing any additional diagnostic procedures related to evaluating the presence or absence of cancer-associated mutations in the subject's tumors, evaluating potential effectiveness of the treatments for the subject's cancer as well as recommending or performing such treatments, monitoring the subject's cancer, or any other steps or processes related to treatment or diagnosis of a cancer.

The expressions "detect in blood," "detection in blood," "detecting in blood," and the related expressions, as used herein, refer to the act or the result of finding or discovering nucleic acid sequences in a sample of the liquid fraction of blood, such as plasma or serum.

The term "local metastasis" to a process or a result of a process, in which cancer cells originating from a cancerous tumor penetrate and infiltrate surrounding normal tissues in the local area, typically in the same or adjacent organ or organs, forming new tumor. For example, "local metastasis" metastatic stage of NSCLC means that metastasis is present, but no metastasis is detected in extrathoracic organs. In reference to NSCLC, the term "local metastasis" encompasses the metastatic stage "M1a."

The term "distant metastasis" refers to a process or a result of a process, in which cancer spreads to tissues and organs that are distant from the primary tumor site. For example, the term "distant metastasis" used in the context of NSCLC means that metastasis is present and is detected in extrathoracic organs. In reference to NSCLC, the term "distant metastasis" encompasses the metastatic stage "M1b."

The terms "detect," "detecting," "detection," "and similar terms are used in this document to broadly to refer to a process or discovering or determining the presence or an absence, as well as a degree, quantity, or level, or probability of occurrence of something. The terms necessarily involve a physical transformation of matter such as nucleic acid amplification. For example, the term "detecting" when used in reference to EGFR mutation, can denote discovery or determination of the presence, absence, level or quantity, as well as a probability or likelihood of the presence or absence of the EGFR mutation. It is to be understood that the expressions "detecting presence or absence," "detection of presence or absence" and related expression, when used in reference to tumor-associated mutations, include qualitative and quantitative detection. Quantitative detection includes the determination of level, quantity or amounts of mutated nucleic acid sequences in the sample, on which the detection process is performed.

The term "mutation" or "mutated sequence," when used in reference to nucleotide or amino acid sequence can be used interchangeably with the terms "variant," "allelic variant," "variance," or "polymorphism." For example, the phrases "detecting a mutation," "detecting a mutated sequence" "detecting polymorphism" or "detecting sequence variance" can be used interchangeably when discussing the methods of the present invention.

DETAILED DESCRIPTION OF THE INVENTION

Figure 1:
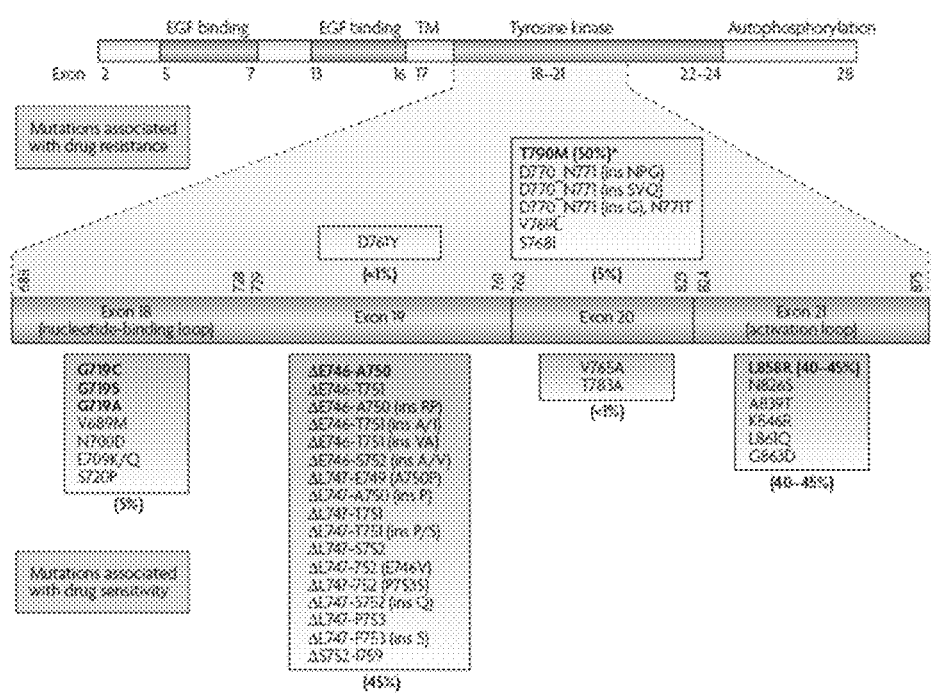
FIG. 1 is a schematic illustration of some known EGFR mutations found in the tyrosine kinase domain of EGFR, adapted from Sharma et al., *Nat. Rev. Cancer*, 7:169 (2007).

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

The inventors have discovered that detection of tumor-associated mutated nucleic acid sequences circulating in the blood of a subject with a solid tumor cancer can be performed quickly and accurately by performing real-time quantitative PCR on the blood sample or on the genomic DNA isolated from a blood sample obtained from the subject with the solid tumor cancer. By improving the methods of processing and analyzing quantitative PCR data, the inventors achieved unexpectedly improved validity of the measurements of tumor-associated mutated nucleic acid sequences circulating in the blood of the subjects with solid tumor cancers. The inventors discovered that a status of a solid tumor cancer in a subject can be advantageously assessed by measuring the type and amount of tumor-associated mutated nucleic acid sequences circulating in the subject's blood. The inventors have also discovered that detection of tumor-associated mutations in subjects with solid tumor cancers based on the detection of mutated nucleic acid sequences circulating in the subjects' blood can be significantly improved if the metastasis status of the cancer in such subjects is taken into account.

Detection of Tumor-Associated Mutations in Blood that Takes into Account Metastatic Status of a Subject In one example, the inventors have discovered that detection of EGFR mutations in NSCLC subjects based on the detection of mutated EGFR sequences circulating in the subjects' blood can be significantly improved if the metastasis status of the NSCLC subjects is taken into account. In particular, the inventors have discovered that in a subset of NSCLC subjects, those subjects having distant metastasis NSCLC, the presence or absence of EGFR mutations detected by amplification of nucleic acid present in blood accurately predicts the presence or absence of EGFR mutations in the subjects' NSCLC tumors. In view of the discovery that blood assays are reliable for subjects with distant metastases, a negative result, i.e., a finding of no EGFR mutations in a blood sample, is sufficient to determine that the subject does not carry the EGFR mutation and therefore does not require an invasive biopsy to confirm the negative results. In contrast, in NSCLC subjects without distant metastasis NSCLC, while the presence of detectable EGFR mutations in blood serves as an accurate predictor of the presence of EGFR mutations in the subjects' NSCLC tumors, the absence of delectable EGFR mutations in blood cannot serve as an accurate predictor of the absence of EGFR mutations in the subjects' NSCLC tumors.

The above discovery can be generally applied to the detection of tumor-associated mutations in the blood of the subjects with solid tumor cancers. Detection of an absence of a tumor-associated mutation in a blood sample obtained from a subject with distant metastasis solid tumor cancer is sufficient to determine the subject does not carry the mutation and therefore does not require any additional procedures, such as an invasive biopsy, to confirm the negative results. In contrast, if a subject has a solid tumor cancer without distant metastasis, detection of a presence of a tumor-associated mutation in blood serves as an accurate predictor of the presence of the mutations in the subjects' tumors, while detection of the absence of a delectable mutation in blood cannot serve as an accurate predictor of the absence of the mutation in the subjects' tumors. Accordingly, described herein are methods that detect the presence or absence of tumor-associated mutations in the blood of a subject with a solid-tumor cancer, in order to assess the subject's status. Some embodiments of the above methods are the methods that detect the presence or absence of mutations in epidermal growth factor receptor (EGFR) in the blood of a subject with non-small cell lung cancer (NSCLC), in order to assess the subject's status.

Tumor-associated mutations can affect the effectiveness of cancer treatments. For example, tumor EGFR mutations influence the effectiveness of certain NSCLC treatments, such as therapies targeting EGFR, for example, tyrosine kinase inhibitor therapies, including, but not limited to, erlotinib and gefitinib. By using the methods described herein, the mutation status of the cancerous tumors in the subject can be accurately assessed and applied to the decision-making process on selection and administration of appropriate therapy, if any exists, or additional diagnostic procedures.

Before the discoveries described herein, high false negative error rate limited application of blood-based detection of tumor-associated mutations in a clinical and diagnostic context, since it necessitated additional testing of tumor tissue of the patients found mutation-negative based on the blood samples. Some embodiments of the methods described herein address the above problem by discriminating solid-tumor subjects based on their metastasis status. In particular, the methods described herein incorporate and apply the discovery that the high false negative rate observed in the previously described blood-based diagnostic procedures is not observed among the subjects with metastatic NSCLC distant metastasis (e.g., M1b metastasis status). Blood detection of EGFR mutations in M1b metastasis status NSCLC subjects can therefore be used as a reliable diagnostic procedure for NSCLC monitoring and in determining further course of diagnosis and treatment of NSCLC.

The embodiments of methods described herein are not limited to diagnosis and treatment of NSCLC subjects, but are generally applicable to diagnosis and treatment of the subjects with various solid-tumor cancers. Furthermore, embodiments of the methods described herein are not limited to the subjects with distant metastasis solid-tumor cancer. According to some embodiments of the methods described herein, the status of the solid-tumor in the subject without distant metastasis can also be assessed. The assessment involves inferring whether or not the subjects' tumor tissue contains mutations detected in the blood using the following criteria. The presence of the mutated sequence in the blood of the subject with a solid tumor cancer but without distant metastasis indicates a high likelihood that the subject's tumor tissue contains the mutations detected in the blood. Therefore, if mutant sequences are detected in a blood of a subject without distant metastasis (such as in a subject with no metastasis or only local metastasis), further diagnostic and treatment decisions can be made based on the high likelihood of the presence of the mutations in the subject's tumor. However, the absence of the sequence in the blood of the subject with solid tumor cancer but without distant metastasis does not reliably indicate that the subject's tumor tissue does not contain the mutations detected in the blood. If mutant sequences are not detected in a blood of such a subject, then additional diagnostic procedures are warranted to ascertain the presence of mutations in the subject's tumors.

For example, when the above embodiments of the methods of assessing a status of a subject with a solid-tumor cancer are applied to NSCLC subjects, the following decision-making process can be performed. The presence of the mutated EGFR sequence in the blood of the subject with NSCLC but without distant metastasis indicates a high likelihood that the subject's NSCLC tumor tissue contains the EGFR mutations detected in the blood. Therefore, if EGFR mutant sequences are detected in a blood of a subject without metastatic NSCLC of stage M1b, further diagnostic and treatment decisions can be made based on the high likelihood of the presence of the EGFR mutations in the subject's tumor. However, the absence of the sequence in the blood of the NSCLC subject without distant metastasis does not reliably indicate that the subject's NSCLC tumor tissue does not contain the EGFR mutations detected in the blood. If EGFR mutant sequences are not detected in a blood of such a subject, then additional diagnostic procedures are warranted to ascertain the presence of mutations in the subject's NSCLC tumors.

Methods of Monitoring a Solid Tumor Cancer in a Subject by Detecting Tumor-Associated Mutated Sequences in the Subject's Blood The methods of assessing status of a subject with a solid-tumor cancer described herein include diagnostic methods that use detection of tumor-associated mutations in a blood of a subject to monitor status and progression of the solid-tumor cancer in the subject. Included within the embodiments of the above methods are the diagnostic methods that use detection of EGFR mutations in a blood of a NSCLC subject to monitor NSCLC status and progression in the subject.

The determination according to the above methods can be an in vitro determination performed on a blood or plasma sample extracted from the subject. The determination can be useful for monitoring cancer therapy effects and making decisions on cancer therapy selection. For example, the methods described herein can be used before, during and/or after tumor-removal surgery on a subject, to monitor the surgery's effectiveness. The methods can also be used before, during, or after any cancer therapy. For example, the methods can be used prior to a cancer therapy to determine the likelihood of the effectiveness of the therapy in a particular subject, or identifying a subject as a suitable candidate for a cancer therapy. The methods can be used during or after cancer therapy to determine the therapy's effectiveness as well as to monitor the emergence of resistance to cancer therapy. The methods can also be used during cancer remission to monitor cancer recurrence and progression.

In some embodiments, the methods employ qualitative detection of tumor-associated mutations to determine the presence or absence, or the nature of tumor-associated mutations in the blood of the subjects. In some embodiments, the methods employ quantitative determination of tumor-associated mutations to determine the amount of mutated sequences present in the subject's blood. Qualitative or quantitative determination, or combination thereof, can be referred to as determination or detection of a "mutation load," and can be used to assess the status of a solid-tumor cancer in the subject, including the severity of the cancer. Mutation load of tumor-associated mutation in a blood of a subject can be characterized by the number of tumor-associated mutations in the subject's blood (that is, how many different mutations are detected), amount of-tumor associated mutations detected in the subject's blood (quantity of the mutated tumor-associated nucleic acids circulating in the subject's blood), or a combination of the foregoing. It is to be understood that, in some cases, a mutation load of tumor-associated mutations detected in the blood of a subject with a tumor-associated cancer correlates with the cancer's severity and/or progression in a subject. Mutation load can also correlate with the effectiveness or lack thereof of cancer therapies administered to the subject.

In one embodiment of the methods of monitoring a solid tumor cancer described herein, the mutation load being detected is quantity of at least one activating tumor-associated mutation and at least one resistance tumor-associated mutation in a blood sample obtained from a solid cancer patient. The mutation load is being detected over time, for example, during a course of cancer therapy or therapies. The detected quantity of the at least one activating tumor-associated mutation serves as an indicator of cancer progression, severity, and/or a success or lack thereof of the therapy or the therapies administered to the patient. The detected quality of the at least one resistance mutation serves an indicator of cancer progression, severity, resistance to the therapy or therapies being administered to the patient. The decision-making process on the treatment of the solid-tumor cancer in the patient is performed based on the mutation load being detected.

Unexpectedly, by applying the methods described herein, progression, severity or stage of a solid-tumor cancer in a patient, as well as susceptibility of the cancer to certain therapies, can be reliably recognized or determined before the emergence of clinical signs or symptoms in the subject, or before the signs or symptoms become detectable by conventional detection techniques and procedures. In some cases, the status of a solid tumor cancer in a subject can be assessed one or more (meaning 1, 2, 3, 4, 5, 6, 7, 8, 9, 10, 11, 12, 13, or any interval delineated by these integers) weeks or months before the emergence of clinical or conventionally detectable sign or symptoms of solid tumor cancer in the subject. Clinical decisions can therefore be made based on the tumor-associated mutation load found in the subject's blood. For example, a cancer therapy can be started, stopped or changed based the subject's detected mutation load. In another example, a cancer therapy dose can be adjusted, such as increased or decreased, based on the subject's tumor-associated mutation load. The methods of monitoring a solid tumor cancer described herein advantageously reduce or minimize the number of complex, expensive or invasive diagnostic procedures performed on a solid tumor cancer patient, while at the same time providing diagnostic data for informed clinical decision making process. In some cases, the methods of monitoring a solid tumor cancer described herein can replace more expensive and/or invasive diagnostic procedures, such as biopsies. The methods of monitoring a solid tumor cancer described herein can lower the cost of cancer treatment and diagnostics, decrease patient discomfort, and lead to more accurate clinical decision making process, which may lead to more favorable cancer treatment outcomes.

In one illustrative example, the mutation load of EGFR mutations in a blood of a subject with NSCLC is determined and used in a clinical decision-making process. Targeted EGFR therapy is indicated and administered to the subject based on the detected presence of one or more activating EGFR mutations in the subject's blood. The dose of the targeted EGFR therapy is determined based on the activating EGFR mutation load. For example, higher dose of the targeted EGFR therapy with a reversible tyrosine kinase inhibitor ("reversible TKI therapy") can be recommended based on the higher mutation load. The status of the NSCLC subject is monitored during the course of the reversible TKI therapy. Decrease or, in some cases, maintenance of the activating EGFR mutation load indicates a success of the reversible TKI therapy, indicating that it can be continued or, in some cases, stopped. Increase in EGFR mutation load indicates a decrease in the effectiveness of the reversible TKI therapy. Emergence of the resistance EGFR mutations or increase of resistance EGFR mutation load also indicates a decrease or a potential decrease in the effectiveness of the reversible TKI therapy. When a decrease or potential decrease in the effectiveness of the TKI therapy is detected, various clinical decisions can be made, such as increasing the dosage of the reversible TKI therapy, administering a different therapy, such as chemotherapy and/or radiotherapy, administering a different targeted therapy, such as an irreversible TKI therapy, or any combination of the foregoing.

Improved Detection of Tumor-Associated Mutations

In the embodiments of the methods described herein, nucleic acid sequences are detected by suitable methods, such as quantitative amplification. Methods of quantitative amplification are disclosed in, e.g., U.S. Pat. Nos. 5,210,015; 5,804,375; 6,127,155; 6,180,349; 6,033,854; and 5,972,602, as well as in, e.g., Holland et al., *Proc. Natl. Acad. Sci.* 88:7276-7280 (1991), Gibson et al., *Genome Research* 6:995-1001 (1996); DeGraves, et al., *Biotechniques* 34(1): 106-10, 112-5 (2003); Deiman B, et al., *Mol Biotechnol.* 20(2):163-79 (2002). Amplifications may be monitored in "real time."

In some embodiments of the methods described herein, quantitative PCR is employed. Quantitative PCR refers generally to a method that allows for quantification of the amounts of the target nucleic acid sequence used at the start at the PCR reaction. Quantitative PCR techniques use various approaches to quantification. One example of a quantitative PCR method is "real time PCR," which can be also referred to as "real time quantitative PCR." Although some sources use the terms "real time PCR" and "quantitative PCR" synonymously, this is not the case for the present document. Here, the term "quantitative PCR" encompasses all PCR-based techniques that allow for quantification of the initially present target nucleic acid sequences. The term "real time PCR" is used to denote a subset of quantitative PCR techniques that allow for detection of PCR product throughout the PCR reaction, or in real time, the principles of real-time PCR are generally described in Holland et al. (1991) and Held et al. "Real Time Quantitative PCR" Genome Research 6:986-994 (1996). Generally, real-time PCR measures a signal at each amplification cycle. Conventional real-time PCR techniques rely on fluorophores that emit a signal at the completion of every multiplication cycle. Examples of such fluorophores are fluorescence dyes that emit fluorescence at a defined wavelength upon binding to double-stranded DNA, such as SYBR green. An increase in double-stranded DNA during each amplification cycle thus leads to an increase in fluorescence intensity due to accumulation of PCR product. Another example of fluorophores used in real-time PCR is sequence-specific fluorescent reporter probes. The examples of such probes are TaqMan® probes and FRET probes. TaqMan® probes contain a fluorophore and a fluorescence quencher, which reduces the fluorescence emitted by the fluorophore. During the extension phase of PCR, the probe is cleaved by the exonuclease activity of the DNA polymerase, releasing the fluorophore. The fluorophore release results in an increase in fluorescence signal, which is proportionate to the amount of the PCR product. FRET probes employ fluorescence resonance energy transfer (FRET). Two labeled sequence-specific probes are designed to bind to the PCR product during the annealing phase of PCR, which results in an energy transfer from a donor fluorophore to an acceptor fluorophore. This results in an increase in fluorescence during the annealing phase, which is proportional to the amount of the PCR product.

The use of sequence-specific reporter probe provides for detection of a target sequence with high specificity, and enables quantification even in the presence of non-specific DNA amplification. Fluorescent probes can also be used in multiplex assays—for detection of several genes in the same reaction—based on specific probes with different-colored labels. For example, a multiplex assay can use several sequence-specific probes, labeled with a variety of fluorophores, including, but not limited to, FAM, JA270, CY5.5, and HEX, in the same PCR reaction mixture.

One example of a multiplex assay that can be suitably employed for detection of mutated EGFR sequences according to the methods of the present invention is allele-specific PCR, such the assay that can be performed with the COBAS® EGFR Mutation Test kit (Roche Molecular Diagnostics, Indianapolis, Ind.), which employs allele-specific EGFR primers to detect mutations in nucleic acid sequences in the presence of wild-type variants of the sequences. Allele-specific PCR is a technique in which the variant of the nucleic acid sequence present in the PCR reaction mixture is selectively amplified and detected. Allele-specific PCR employs at least one "allele-specific primer." The term "allele-specific" primer generally refers to a primer whose extension occurs in a PCR reaction only when a specific variant of a nucleic acid sequence is present in the reaction mixture. In other words, allele-specific primers are designed in such a way that they discriminate between variants of nucleic acids and selectively multiply nucleic acid templates that include a variant to be detected.

Some embodiments of the methods described herein employ improved detection methods of tumor-associated mutations in blood samples obtained from the a subject with a solid tumor cancer. In one example, the step of detecting one or more EGFR mutations in a blood of a subject with NSCLC comprises detection of one or more mutated NSCLC nucleic acid sequences in a sample obtained from the subject. The detection may comprise contacting the sample or nucleic acids isolated from the sample, such as total genomic DNA, with one more allele-specific primers and other components of a PCR, such as enzymes and nucleotides, incubating the resulting reaction mixture under the conditions allowing for selective amplification of the mutated nucleic acid sequences, and detecting the presence of the amplified product. Allele-specific PCR can be combined with real-time quantitative PCR in the embodiments of the methods described herein to improve the detection of the of the mutated tumor-associated nucleic acid sequences.

Conventional methods of detecting tumor-associated mutations in blood samples typically employ additional steps for increasing the content of the mutated sequences in the sample prior to performing PCR amplification of the mutant sequences. For example, in one conventional method, isolation of tumor cells from the subject's blood sample prior to PCR amplification is performed to improve the sensitivity of detection of tumor-associated mutations. In another conventional method, non-mutated DNA sequences corresponding to the mutated tumor-associated sequences are subjected to nuclease digestion prior to PCR amplification in order to minimize the background of the non-mutated sequences. Disclosed herein are improved detection methods, which employ quantitative PCR, and can detect tumor-associated mutations in blood samples obtained from the subjects with solid-tumor cancers, and, advantageously, do not require additional steps for isolating tumor cells, tumor DNA, or increasing the content of the mutated sequences in the sample prior to performing real-time quantitative PCR.

As discussed above, real-time PCR relies on detection of a measurable parameter, such as fluorescence, during the course of the PCR reaction. The amount of the measurable parameter is proportional to the amount of the PCR product, which allows observe the increase of the PCR product "in real time." Some real-time PCR methods allow for quantification of the input DNA template based on the observable progress of the PCR reaction. The analysis and processing of the data involved is discussed below. A "growth curve" or "amplification curve" in the context of a nucleic acid amplification assay is a graph of a function, where an independent variable is the number of amplification cycles and a dependent variable is an amplification-dependent measurable parameter measured at each cycle of amplification, such as fluorescence emitted by a fluorophore. Typically, the amplification-dependent measurable parameter is the amount of fluorescence emitted by the probe upon hybridization, or upon the hydrolysis of the probe by the nuclease activity of the nucleic acid polymerase, see Holland et al., (1991) *Proc. Natl. Acad. Sci.* 88:7276-7280 and U.S. Pat. No. 5,210,015. In a typical polymerase chain reaction, a growth curve comprises a segment of exponential growth followed by a plateau, resulting in a sigmoidal-shaped amplification plot when using a linear scale. A growth curve is characterized by a "cross point" value or "$C_p$" value, which can be also termed "threshold value" (or $C_t$ value) which is a number of cycles where a predetermined magnitude of the measurable parameter is achieved. A lower $C_p$ value represents more rapid completion of amplification, while the higher $C_p$ value represents slower completion of amplification. Where efficiency of amplification is similar, the lower $C_p$ value is reflective of a higher starting amount of the target nucleic acid, while the higher $C_p$ value is reflective of a lower starting amount of the target nucleic acid. Where a control nucleic acid of known concentration is used to generate a "standard curve," or a set of "control" $C_p$ values at various known concentrations of a control nucleic acid, it becomes possible to determine the absolute amount of the target nucleic acid in the sample by comparing $C_p$ values of the target and control nucleic acids.

The accuracy of the detection by real-time quantitative PCR therefore depends on correct selection of a number of parameters. One parameter that needs to be correctly determined is the range in which $C_p$ values bear linear correlation with the starting amount of the nucleic acid, expressed in log copy number. This range can be termed "valid range" or "assay linearity range" of the real-time PCR assay.

The inventors have found that a blood sample containing genomic DNA not generally known to contain a tumor-associated mutation may nevertheless generate an amplification signal at some genomic DNA concentrations. In some embodiments, this background level of signal is therefore a cutoff below which a signal must fall to be valid, i.e., to be considered different from the background. As noted above, the level of background amplification changes with concentration of genomic DNA. Accordingly, in some embodiments, determination of the presence or absence of a tumor-associated mutation comprises comparison of a threshold value to a control value, wherein the control value is dependent, and varies based upon the concentration of genomic DNA in the sample. Thus, if the cycle threshold for the sample is below the control value then the sample is considered to contain the tumor-associated mutation and if the cycle threshold of the sample is equal to or higher than the control value, the result does not indicate the presence of the tumor-associated mutation, and can be referred to as "negative result"). In some embodiments, such as the testing of NSCLC pM1b metastatic stage patients for an EGFR mutation, such a negative result is indicative, with high likelihood, of the absence of an EGFR mutation in the patients' tumors. In some other embodiments, such as testing of NSCLC patients of a metastatic stage other than pM1b (such as M0 or pM1a), for an EGFR mutation, such a negative result may not be indicative of the absence of an EGFR mutation in the patients' tumors, and re-testing of the patients' tumor tissue should be considered.

In some embodiments, the control value is the highest $C_p$ value or range at which non-specific amplification in the absence of the target DNA occurs, and can be referred to as a "breakthrough" value. In some embodiments, the control value is in fact a range of values, within which a positive value from a sample must fall in order to be considered. Said another way, the range represents possible signal levels outside the typical range of background signal. In some embodiments, the control range is between the above-described breakthrough value and the cycle threshold value of a positive control. In some embodiments, the control value is based on amplification of an internal control, for example another region of the mutated locus that is not mutated frequently.

The improved real-time quantitative PCR methods described herein establish the valid cycle-threshold ($C_t$) range by generating standard curves for control DNA at various levels of genomic DNA in the real-time PCR reaction mixture and selecting the valid cycle-threshold range based on range in which assay linearity is observed. A control or cut-off value for the quantitative real-time PCR reaction is determined according to some other embodiments of the improved methods described herein, below which the non-specific amplification in the absence of the target DNA is not likely to interfere with the quantitative detection of the target DNA present in the reaction mixture. In some other embodiments, the improved methods described herein employ a calibration curve for quantification of a target DNA present in the reaction mixture which takes into account various amounts of genomic DNA present in the sample. Various combinations of improvements of real-time PCR assays discussed above can be incorporated into the improved methods of detection of tumor-associated mutations in blood samples, or another target locus in genomic DNA, thus leading to unexpectedly increased accuracy of such detection.

The calculations and comparisons (e.g., of a sample signal to a control value or range) for the methods described herein can involve computer-based calculations and tools. Tools can be advantageously provided in the form of computer programs that are executable by a general purpose computer system (referred to herein as a "host computer") of conventional design. The host computer may be configured with many different hardware components and can be made in many dimensions and styles (e.g., desktop PC, laptop, tablet PC, handheld computer, server, workstation, mainframe). Standard components, such as monitors, keyboards, disk drives, CD and/or DVD drives, and the like, may be included. Where the host computer is attached to a network, the connections may be provided via any suitable transport media (e.g., wired, optical, and/or wireless media) and any suitable communication protocol (e.g., TCP/IP); the host computer may include suitable networking hardware (e.g., modem, Ethernet card, WiFi card). The host computer may implement any of a variety of operating systems, including UNIX, Linux, Microsoft Windows, MacOS, or any other operating system.

Computer code for implementing aspects of the present invention may be written in a variety of languages, including PERL, C, C++, Java, JavaScript, VBScript, AWK, or any other scripting or programming language that can be executed on the host computer or that can be compiled to execute on the host computer. Code may also be written or distributed in low level languages such as assembler languages or machine languages.

The host computer system advantageously provides an interface via which the user controls operation of the tools. In the examples described herein, software tools are implemented as scripts (e.g., using PERL), execution of which can be initialed by a user from a standard command line interface of an operating system such as Linux or UNIX. Those skilled in the art will appreciate that commands can be adapted to the operating system as appropriate. In other embodiments, a graphical user interface may be provided, allowing the user to control operations using a pointing device. Thus, the present invention is not limited to any particular user interface.

Scripts or programs incorporating various features of the present invention may be encoded on various computer readable media for storage and/or transmission. Examples of suitable media include magnetic disk or tape, optical storage media such as compact disk (CD) or DVD (digital versatile disk), flash memory, and carrier signals adapted for transmission via wired, optical, and/or wireless networks conforming to a variety of protocols, including the Internet.

General Considerations Applicable to the Embodiments of the Present Invention

A subject having a solid-tumor cancer, such as NSCLC, can have the solid-tumor cancer that was not diagnosed prior to the performance of the methods according to the embodiments of the present invention. For example, a subject can be tested for the presence of a tumor-associated mutation, such as EGFR mutant sequences, in blood before or during completion of other diagnostic procedures meant to diagnose the solid-tumor cancer. Examples of such diagnostic procedures are various imaging techniques or histological analysis of samples obtained during biopsy. Similar considerations apply to metastatic status and cancer staging of the subjects with solid-tumor cancer. Metastatic status, such as M1a or M1b status of NSCLC, and cancer staging can be determined before, concurrently with or subsequently to the methods according to the embodiments of the present invention, which are not limited by the order of various diagnostic steps and procedures performed on the subject.

The methods described herein can employ suitable diagnostic procedures in addition to detection of mutated tumor-associated sequences in the subject's blood, in order to accurately assess the status of the solid-tumor cancer in the subject. Additional diagnostic procedures are suitably selected to improve the accuracy of the assessment of the solid-tumor cancer in the subject, and can include, but are not limited to, various imaging techniques, biopsies, histological analysis, sequence analysis and other procedures.

The methods described herein are not limited to purely diagnostic procedures, but can incorporate various treatment steps, thus embodying application and use of the diagnostic discoveries described herein to improved methods of treating solid tumor cancers, one example of which is NSCLC. In one embodiment, the appropriate cancer treatments and diagnostic procedures are suitably selected and administered or performed based on the presence or absence of tumor-associated mutations in the blood of a subject with a solid tumor cancer, such as the presence or absence of tumor-associated EGFR mutations detected in the blood of NSCLC subject. Cancer treatments described herein can include surgical or non-invasive treatments, such as drug or radiation therapies.

Tumor-Associated Mutations

Tumor-associated mutations that are detected according to the methods described herein are mutations that are found in tumors of subjects with solid tumor cancers and affect development of the solid tumor cancers in the subjects. For example, tumor-associated mutations can affect the emergence, progression or recurrence of the cancer, as well as the responsiveness or susceptibility of the cancer to a cancer therapy. One example of tumor-associated mutations that can be detected according to the methods described herein is the mutations in proto-oncogenes that convert them into oncogenes. Another example is the mutations in tumor-suppressor gene that result in the loss or decrease of their function. The mutations that can be detected according to the methods of the present invention are not limited to the mutations in protein-encoding genes, but can also include the mutations in non-coding nucleic acid sequences, such as regulatory elements, sequences encoding non-coding RNA, and other non-coding sequences. Tumor-associated mutations of the protein-coding nucleic acid sequences can be in-frame deletions or insertions, as well as substitutions. For example, mutated EGFR sequences being detected are typically nucleic acid sequences that contain one or more in-frame nucleotide deletions or insertions, as well as nucleotide substitutions that result in mutated amino acid sequence of EGFR. Tumor-associated mutations can result in protein fusions. Some examples of tumor-associated mutations that can be detected in patient's blood and used to monitor cancer emergence, progression, recurrence, as well as to monitor cancer therapy, include without limitation, the following mutations: EGFR mutations, KRAS mutations, including mutations in KRAS codons 12, 13, 61 and 146, ALK mutations, including ALK fusions, ROS1, including ROS1 fusions, c-MET mutations, PIK3CA (PI3K-CA) mutations, NRF2 mutations, FGFR1-3 mutations, AKT1 mutations, including AKT1 fusions, BRAF mutations, including V600E substitution, NRAS mutations, TMPRSS2:ERG fusion, SPOP mutations, RET fusions, PPAR-gamma fusions, IDH-1 mutations, and IDH-2 mutations. It is to be understood that some of the above mutations are associated with some, but not necessarily all, of the solid-tumor cancers. Accordingly, detection of some of the above tumor-associated mutations can be more suitable for assessment of certain cancers. For example, detection of the following mutations can be suitable for assessment of lung cancer: EGFR mutations, KRAS mutations, ALK fusions, ROS1 fusions, c-MET mutations, PIK3CA (PI3K-CA) mutations, NRF2 mutations and FGFR1-3 mutations. In another example, detection of AKT1 mutations, including fusions, can be suitable for assessment of breast cancer. In one more example, detection of KRAS mutations, such as mutations of codons 12, 13, 61 and 146, BRAF substitution V600E, NRAS mutations, PIK3CA (PI3K-CA), EGFR extracellular domain hot spot mutations can be used for assessment of colorectal cancer. Detection of TMPRSS2:ERG fusion and SPOP mutations can be used for assessment of prostate cancer. Detection of BRAF mutations, NRAS mutations, RET fusion and PPAR gamma fusion can be used for assessment of thyroid cancer. Detection of mutations in IDH-1 and IDH-2 can be used for assessment of glioblastoma, while detection of mutations in FGFR3 can be used for detection of bladder cancer. It is to be understood that the above list of the associations of the tumor-associated mutations and types of cancers is not exhaustive or limiting.

Non-Small Cell Lung Cancer

Lung cancer is a solid tumor cancer that forms in lung tissue. Most of the lung cancer begins in the epithelial cells lining air passages. This type of cancer is termed "Non-Small Cell Lung Cancer" (NSCLC). The other, less prevalent, type of lung cancer is termed "Small-Cell Lung Cancer," which begins in the non-epithelial lung cells, such as nerve cells or hormone-producing cells. The classification of the lung cancer into NSCLC and small cell is important for determining an appropriate treatment. Lung cancer is also described in terms of staging, which describes the extent of cancer in a patient's body. In the current clinical practice, lung cancer is typically staged according to Classification of Malignant Tumors (TNM), developed and maintained by the International Union Against Cancer (UICC). TNM classification takes into account the size of the tumor and whether it has invaded nearby tissue, involvement of regional lymph nodes, and distant metastasis, or spread of cancer from one body part to another. According to current TNM classification of lung cancer is divided into five stages. Stage 0 is also called in situ lung cancer, meaning that the cancer did not invade tissues outside the lung. Stage I lung cancer is a small tumor that has not spread to any lymph nodes and cam be completely surgically removed. Stage I is divided into two sub-stages, A and B, based on the size of the tumor. Small tumors, such as those less than 3 cm are classified as stage IA. Stage I tumors between 3 and 5 cm are typically classified as stage IB lung cancer. Stage II typically refers to larger tumors, with sub-stage IIA describing the tumors larger tumor (over 5 cm but less than 7 cm wide) that has spread to the lymph nodes or a larger tumor (more than 7 cm wide) that may or may not have invaded nearby structures in the lung but has not spread to the lymph nodes.

When lung cancer metastasizes, it spreads through blood or lymph vessels after breaking away from a lung tumor. Stage III describes the cancer Tumors that are difficult to remove, because they spread to the tissues outside of the lung. Stage III cancers are classified as either stage IIIA or IIIB. For many stage IIIA cancers and nearly all stage IIIB cancers, the tumor is difficult, and sometimes impossible, to remove. For example, stage IIIB lung cancer may spread to the lymph nodes located in the center of the chest, or invade nearby structures in the lung. Stage IV typically describes lung cancer that has spread to more than one area in the other lung, the fluid surrounding the lung or the heart, or distant parts of the body by the process of metastasis. The terms "stage IVA" can be used to describe lung cancer that spread within the chest, while the term "stage IVB" when it has spread outside of the chest. In general, surgery is not successful for most stage III or IV lung cancer. Lung cancer can also be impossible to remove if it has spread to the lymph nodes above the collarbone, or if the cancer has grown into vital structures within the chest, such as the heart, large blood vessels, or the main breathing tubes leading to the lungs. Stage III and IV lung cancer can be described as "late stage lung cancer" or "advanced lung cancer."

Late stage or advanced lung cancer can be characterized in terms of its metastatic status or metastatic stage. For example, so-called metastasis stages M0 and M1 can be used to refer to the cancer's metastatic status. M0 metastatic status typically indicates that no metastasis of a lung tumor is detected in a patient. M1 status typically indicates that metastasis is detected. M1 metastatic status can be further subdivided into stages M1a and M1b. Metastatic stage M1a is typically used to describe metastatic lung cancer in which separate tumor nodule or nodules appear in a contralateral lung lobe, lung cancer tumors with pleural nodules or malignant pleural or pericardial effusions. Metastatic status of NSCLC cancer in a subject can be determined by various diagnostic procedures, including imaging techniques, such as PET scanning, or histological examinations of tissue samples obtained by biopsy. Metastatic stage M1b is typically used to describe lung cancer with distant metastasis in extrathoracic organs.

Epidermal Growth Factor Receptor

Epidermal Growth Factor Receptor (EGFR), which is also, known as HER-1 or Erb-B1, is an oncogene involved in development and progression of NSCLC in some patients. EGFR is a membrane-bound receptor protein of Erb family. EGFR comprises an extracellular ligand-binding domain, a transmembrane domain, and an intracellular domain that possesses tyrosine kinase activity. EGFR is inactive in its monomeric state. Binding of a ligand leads to homo and heterodimerization of EGFR with other HER family members, followed by intermolecular tyrosine phosphorylation. Adaptor or signaling molecules bind to phosphorylated EGFR, which triggers downstream intracellular signaling cascades. Examples of the signaling cascades triggered by EGFR are Akt, STAT and MAPK cascades. EGFR is known to promote growth of various cancers by several mechanisms, including, but not limited to, EGFR amplification, and mutational activation of EGFR.

Anti-cancer therapeutic drugs were developed that inhibit tyrosine kinase inhibitory activity of EGFR. Two of such drugs are small molecules gefitinib and erlotinib, which belong to the class of quinazoline derivatives. Gefitinib and erlotinib were both shown to inhibit EGFR tyrosine phosphorylation. In the clinical studies that led to approval of gefitinib and erlotinib, the drugs were shown to prolong survival in a relatively small subset of non-small cell lung cancer (NSCLC) patients after chemotherapy. Subsequent studies revealed that mutations in EGFR tyrosine kinase domain were present in a portion of NSCLC patients, and that these mutations were associated with clinical responsiveness to gefitinib and erlotinib. EGFR mutations which were associated with resistance to gefitinib and erlotinib were also identified. Discussion of the early developments in the area of EGFR mutations in NSCLC patients and their connection to gefitinib and erlotinib therapies is found, for example, in Pao and Miller, *Journal of Clinical Oncology*, 23:2556-2568 (2005) and Rosell et al., *Clin. Cancer. Res.* 12:7222-7231, incorporated herein by reference. The presence or absence of EGFR mutations in NSCLC patients can therefore serve as a marker suitable for assessing the status of NSCLC in patients, such as determining whether a particular patient's NSCLC is potentially responsive to EGFR-directed therapy.

Known EGFR mutations associated with drug susceptibility or resistance to known targeted drug therapies are generally located in the tyrosine-kinase domain of EGFR. Some of the known mutations are illustrated in FIG. 1, and in Table 1. Some of these mutations are classified into "activating mutations," which are known to enhance EGFR signaling. Some of the activating EGFR mutations are associated with sensitivity to targeted drug therapies, such as tyrosine kinase inhibitor therapies, and are sometimes referred to as "sensitizing" mutations. Examples of such mutations are in frame deletions EGFR exon 19, and some amino-acid substitutions, such as L858R, L86IQ and substitutions at G719, sometimes referred to as G719X, which include, but are not limited to G719A, G719C and G719S.

Other EGFR mutations are associated with resistance to tyrosine kinase inhibitor therapies, and often arise in the course of the therapy. Such mutations can be referred to as "resistance" mutations, examples of which are in frame EGFR exon 20 insertions and T790M and S678I amino acid substitutions. The methods described herein employ detection of EGFR mutations, including activating and resistance mutations, in the blood of a subject with NSCLC.

EXAMPLES

Example 1

Isolation of Nucleic Acids and PCR Amplification

All the samples were acquired from lung cancer (NSCLC) patients. Nucleic acid isolation was performed utilizing COBAS® DNA Sample Preparation Kit (Roche Molecular Diagnostics, Indianapolis, Ind.) according to the manufacturer's instructions. Real-time alleles-specific PCR amplification was performed on a COBAS® instrument using COBAS® EGFR Mutation Test kit (Roche Molecular Diagnostics) according to the manufacturer's instructions. Briefly, the COBAS® kit contains three reaction mixtures, MMX1, MMX2, and MMX3, for allele-specific real-time PCR detecting various mutations in the human EGFR gene. MMX1 comprises primers and 6-carboxyfluorescein (FAM)-labeled probes for multiple deletions in exon 19 of the human EGFR gene (termed Ex19Del) and substitution mutation S768I (JA270 signal). MMX2 comprises primers and probes for substitution mutation L858R (FAM signal) and mutation T790M (JA270 signal). MMX3 comprises, primers and probes for substitution mutation L861Q (FAM signal), a set of substitution mutations G719X (HEX signal) and multiple insertions in exon 20 of the human EGFR gene (Ex20Ins) (JA270 signal). Each reaction further comprises internal control (IC) primers and probes targeting exon 28 of the human EGFR gene (Cy5.5 signal).

Example 2

Establishing a Calibration Curve for the Quantification of DNA Targets

Figure 2:
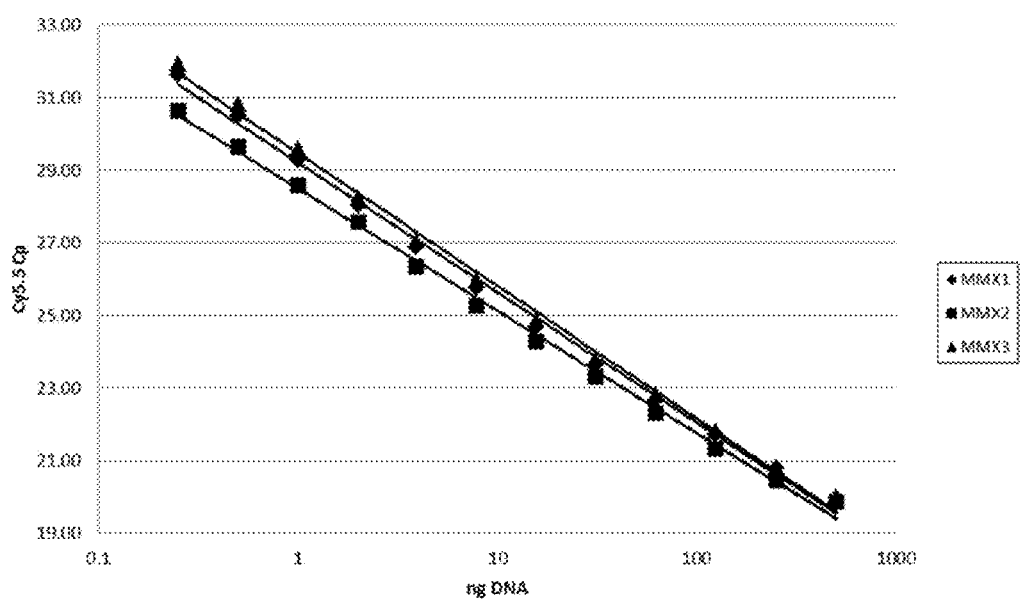
FIG. 2 is a plot illustrating experimental data on real-time PCR cross-point (Cp) values obtained with COBAS® EGFR Mutation Test kit using reaction mixtures MMX1, MMX2 and MMX3 in the presence of different levels of genomic DNA. The X-axis represents genomic DNA level (ng per reaction) and the Y-axis represents cycle number corresponding to the $C_p$ achieved in a reaction.

To calibrate the assay, varying amounts of genomic DNA were subjected to real-time PCR amplification using the COBAS® EGFR Mutation Test kit. Twelve levels of genomic DNA were tested: 0.25, 0.5, 1, 2, 4, 8, 16, 32, 64, 125, 250 and 500 ng/reaction. At each genomic DNA level, 120 replicate PCR assays were run with internal control (IC) primers and probes in three different multiplex PCR reaction mixtures included in the kit (MMX1, 2 and 3, see Example 1). The resulting standard curve is shown in FIG. 2. On FIG. 2, the X-axis represents genomic DNA level and the Y-axis represents cycle number corresponding to the cross point ($C_p$) achieved in the reaction. Based on the experimental data illustrated by FIG. 2, the valid range of the internal control values (IC $C_p$ range) was set at 20-32. In the selected valid $C_p$ range, assay linearity was observed for all the reaction mixtures tested.

Example 3

Establishing a Cut-Off Limit for the Quantitative PCR Assay

For each reaction mixture, a measurable range within the valid IC $C_p$ range was established using the data from non-specific amplification in the absence of the true target occurring at later cycles of PCR, which was termed "breakthrough amplification." For each reaction mixture, breakthrough amplification was observed with at least one set of primers and probes. For each target within each reaction mixture, the value of $C_pR$ was determined, which was the difference between the internal control signal and the breakthrough signal, calculated as the difference between breakthrough $C_p$ and internal control $C_p$ observed in the same reaction. For example, for Ex19del target (illustrated in Table 2), breakthrough occurred at the higher levels of genomic DNA tested, but $C_pR$ was consistently high at these levels. The minimum $C_pR$ observed was selected as a cut-off value. The target Ex19del signal was considered positive (mutation detected) only if the IC value Cp was in the valid range, as discussed in Example 2, and the $C_pR$ value (the difference between the target and the control signal) fell below the cut-off value of 17.7.

Alternatively, the cut-off may be set simply as the lowest breakthrough $C_p$ observed in the calibration example. As illustrated in Table 2, for the S768I target, the target signal was considered positive (mutation detected) only if the IC value was in the valid range and the target $C_p$ value was below the breakthrough threshold of 34 cycles.

Example 4

Figure 3:
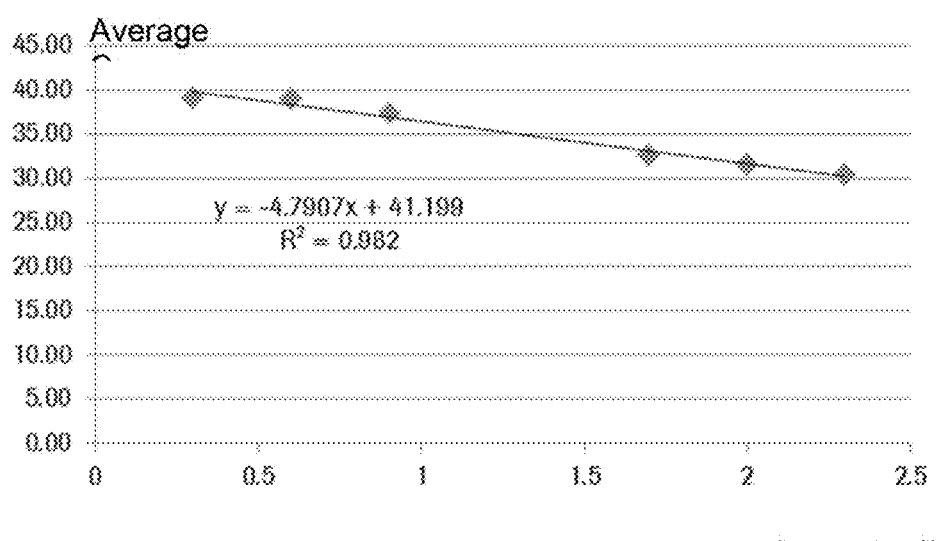
FIG. 3 is a plot schematically showing an exemplary calibration curve for quantification of a target nucleic acid.

Establishing a Calibration Curve for the Quantification of a Mutant Target in the Presence of Wild-Type Genomic DNA Target To approximate patients' samples containing cancer cells and normal cells, as well as genomic DNA, various amounts of each mutant target detectable by the assay (see Example 1) were combined with various amounts of wild-type genomic DNA. Different amounts of the target nucleic acid containing T790M mutation (2, 4, 8, 50, 100, or 200 ng/reaction) were combined with different amounts of wild-type genomic DNA background (0.25, 0.5, 1.0, 2.0, 3.9, 7.8, 15.6, 31.3, 62.5, 125, 250, and 500 ng/reaction). The target-specific $C_p$ obtained in the experiment was then plotted against the amount of input target DNA. The signal for T790M-specific probe (JA270 $C_p$) obtained at different levels of target DNA was averaged and plotted against the log copy number of the T790M mutant target present in the sample. The resulting calibration curve is shown in FIG. 3.

Example 5

Detecting Mutant EGFR DNA in the Blood of Lung Cancer (NSCLC) Patients

Figure 4:
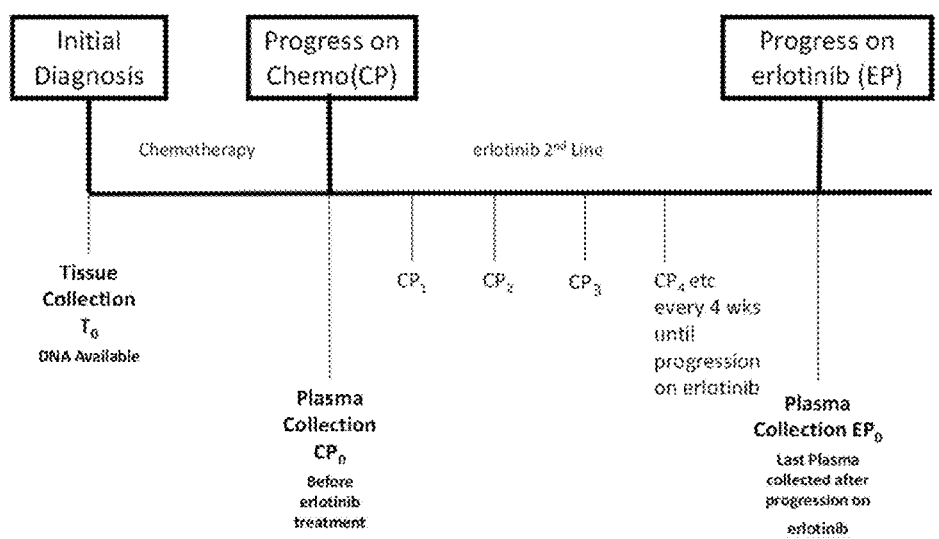
FIG. 4 is a schematic representation of NSCLC treatment timeline and sample collection.
Figure 5:
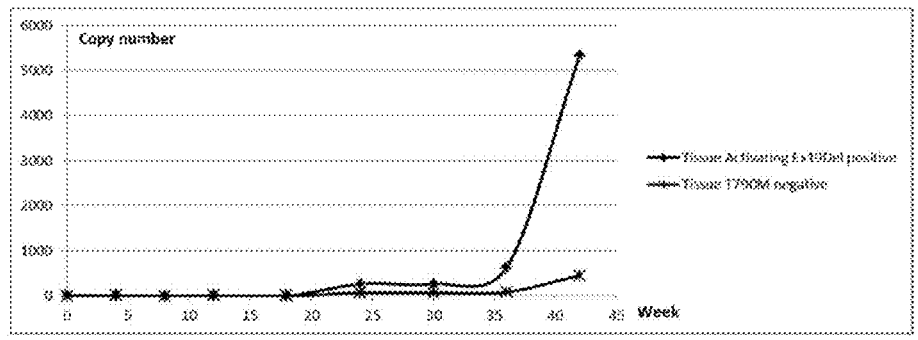
FIG. 5 is a plot illustrating detection of EGFR mutations in the plasma samples of two exemplary NSCLC patients. Week 0 on the X-axis corresponds to time point $CP_0$ before the start of erlotinib treatment in FIG. 3.
Figure 5:
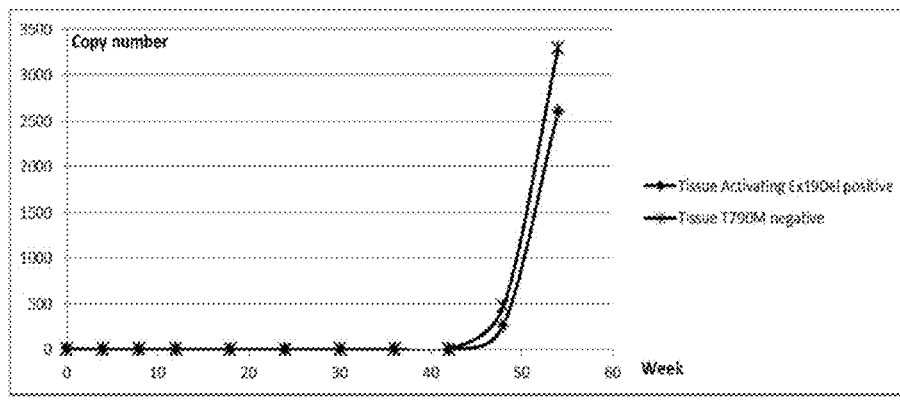

Blood plasma samples were collected from NSCLC patients after they underwent chemotherapy and before and during erlotinib targeted therapy. The timeline of the sample collection is schematically illustrated in FIG. 4. The samples were collected every four weeks at the time points indicated as $CP_{0-4}$ in FIG. 4. Sample collection did not necessarily stop at time point $CP_4$. DNA was isolated from the collected blood plasma samples and subjected to real-time PCR amplification using the COBAS® kits in accordance with manufacturer's instructions (see Example 1). For illustrative purposes, FIG. 5 schematically shows measured levels of an activating exon 10 deletion (Ex19Del) and T790M activating substitution of EGFR in blood plasma of two exemplary patients ("Case A" and "Case B"). In both patients, tissue tumor samples obtained at the initial diagnosis had been previously determined to contain an activating EGFR mutation (Ex19del) but no resistance mutation (T790M). The amount of mutant DNA sequences, expressed in number of copies and plotted on Y-axis of the plot shown in FIG. 5, was measured using the calibration curves described in Example 5. In both cases A and B, increase in the amount of mutant DNA in the blood correlated with progression of NSCLC as detected by suitable imaging techniques and also indicated the rise of resistance to erlotinib therapy.

Example 6

Detection of EGFR Mutations in the Blood of NSCLC Patients with Different Metastasis Statuses Two studies were conducted that correlated detection of EGFR mutations in the blood plasma of NSCLC patients with the patient's metastasis status. In the first study (Study I), plasma samples and matching tissue samples were collected from twenty eight Stage IV NSCLC patients. Mutation status of the tissue and blood samples was determined. The data on the mutations detected in was compared to the metastasis status of the patients. Study I experimental data is summarized in Tables 3 and 4.

In the second study (Study II), plasma samples and matching tissue samples were collected from seventeen Stage IV NSCLC patients. Mutation status of the tissue and blood samples was determined. The data on the mutations detected in was compared to the metastasis status of the patients. Study II experimental data is summarized in Tables 5-I, 5-II and 6.

In both Study I and Study II, it was observed that positive agreement between detection of EGFR mutations in tissue and plasma samples was significantly higher for the patients with distant metastasis (metastatic status pM1b) than for the patient without distant metastasis (metastatic status pM1a). Summary of Study I and Study II data on detection of activating EGFR mutations in blood of NSCLC patients of different metastatic status is schematically shown in Table 7.

Example 7

Figure 6:
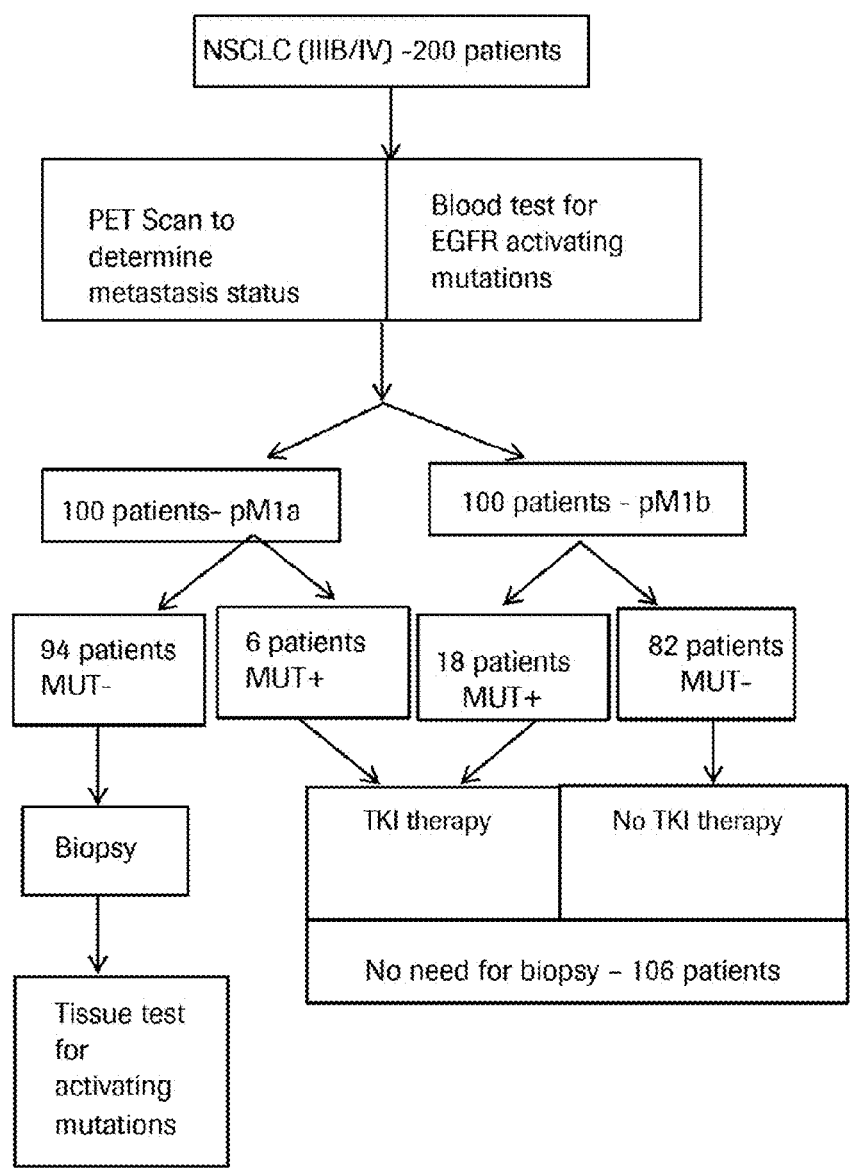
FIG. 6 is a schematic representation of the decision-making process for treatment and diagnosis of patients presenting with NSCLC patients based on blood testing for EGFR activating mutations.

Benefits of Detecting EGFR Mutations in the Blood of Initially Diagnosed NSCLC Patients EGFR activating mutations are detected in blood of 200 patients with initially diagnosed stage IIIB through stage IV NSCLC. The detection is generally performed according to the procedures described in the earlier examples. Activating EGFR mutations are detected in the blood of 20% of the patients. Resistance EGFR mutations are detected in a subset of the patients carrying activating EGFR mutations. Metastasis status of these patients is determined by PET Scan. 50% of the patients are determined to have pM1a metastasis status, and 50% are determined to have pM1b metastasis status. Based on the knowledge of the high positive agreement between detection of the activating EGFR mutations in blood and their presence in tumor tissue in pM1b patients but not in pM1a patient, targeted tyrosine kinase inhibitor (TKI) therapy is recommended for and administered to pM1b and pM1a patients with detectable EGFR activating mutations in blood without additional diagnostic procedures. Targeted TKI therapy is not recommended for pM1b patients without detectable EGFR activating mutations or with detectable resistance mutations in blood (no additional diagnostic procedures are deemed necessary). pM1a patients without detectable EGFR activating mutations in blood are directed to biopsy of the tumor tissue with subsequent mutation detection in the biopsy samples in order to determine whether or not these patients are candidates for EGFR therapy. The above decision-making process for 200 patients is schematically illustrated in FIG. 6. Under this decision-making process, only 94 patients out of 200 need biopsy followed by tissue mutation testing in order to determine whether or not they are candidates for TKI targeted therapy.

Example 8

Benefits of Detecting EGFR Mutations in the Blood of Relapsed NSCLC Patients

EGFR activating mutations are detected in blood of 200 relapse patients with stage IIIB through stage IV NSCLC. The detection is generally performed according to the procedures described in the earlier examples. Activating EGFR mutations are detected in the blood of 20% of the patients.

Figure 7:
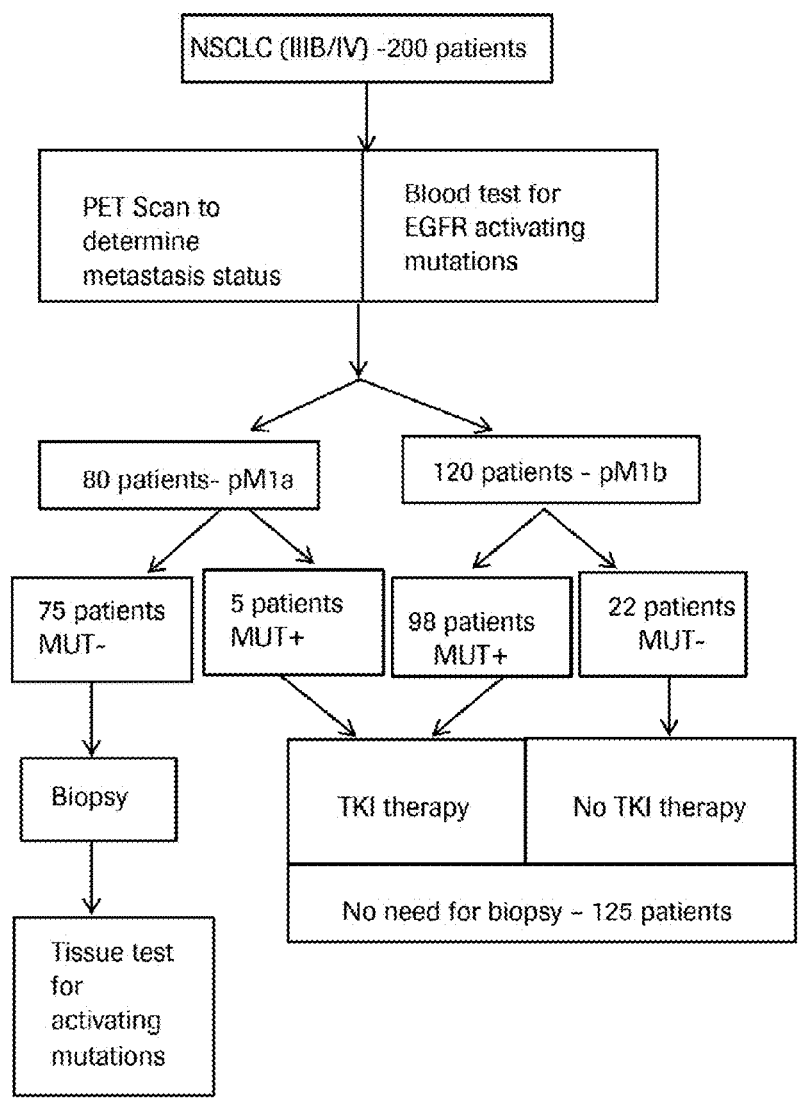
FIG. 7 is a schematic representation of the decision-making process for treatment and diagnosis of relapsing NSCLC patients based on blood testing for EGFR activating mutations.

Metastasis status of these patients is determined by PET Scan. 40% of the patients are determined to have pM1a metastasis status, and 60% are determined to have pM1b metastasis status. Based on the knowledge of the high positive agreement between detection of the activating EGFR mutations in blood and their presence in tumor tissue in pM1b patients but not in pM1a patient, targeted tyrosine kinase inhibitor (TKI) therapy is recommended for and administered to pM1b and pM1a patients with detectable EGFR activating mutations in blood without additional diagnostic procedures. Targeted TKI therapy is not recommended pM1b patients without detectable EGFR activating mutations in blood (no additional diagnostic procedures are deemed necessary). pM1a patients without detectable EGFR activating mutations in blood are directed to biopsy of the tumor tissue with subsequent mutation detection in the biopsy samples in order to determine whether or not these patients are candidates for EGFR therapy. The above decision-making process for 200 patients is schematically illustrated in FIG. 7. Under this decision-making process, only 74 patients out of 200 need biopsy followed by tissue mutation testing in order to determine whether or not they are candidates for TKI targeted therapy.

Example 9

Benefits of Detecting EGFR Mutations in the Blood of NSCLC Patients

Figure 8:
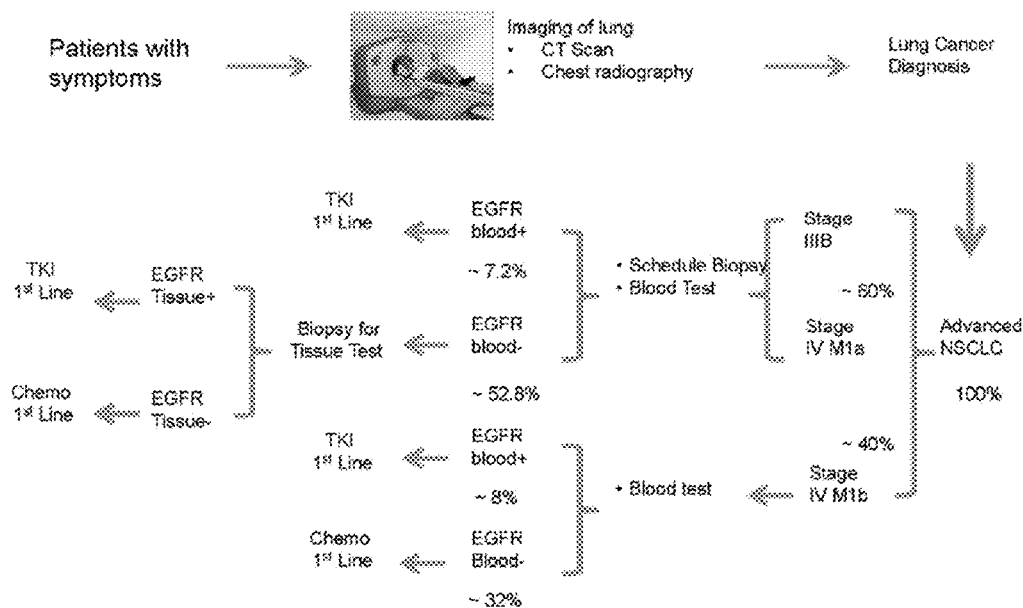
FIG. 8 is a schematic representation of the decision-making process for treatment and diagnosis of NSCLC patients.

EGFR activating mutations are detected in blood of 200 relapse patients with stage IIIB through stage IV NSCLC. The detection is generally performed according to the procedures described in the earlier examples. The decision-making process is schematically illustrated in FIG. 8.

TABLE 1

Examples of EGFR mutations.

| Mutation | Amino Acid Change | Exon |
| --- | --- | --- |
| 2155 G > A | G719S | 18 |
| 2155 G > T | G719C | 18 |
| 2156 G > C | G719A | 18 |
| 2233_2247del15 | K745_E749del | 19 |
| 2235_2248 > AATTC | E746_A750 > IP | 19 |
| 2235_2249del15 | E746_A750del | 19 |
| 2235_2251 > AATTC | E746_T751 > IP | 19 |
| 2235_2252 > AAT | E746_T751 > I | 19 |
| 2235_2255 > AAT | E746_S752 > I | 19 |
| 2236_2250del15 | E746_A750del | 19 |
| 2236_2253del18 | E746_T751del | 19 |
| 2237_2251del15 | E746_T751 > A | 19 |
| 2237_2252 > T | E746_T751 > V | 19 |
| 2237_2253 > TTGCT | E746_T751 > VA | 19 |
| 2237_2254del18 | E746_S752 > A | 19 |
| 2237_2255 > T | E746_S752 > V | 19 |
| 2237_2257 > TCT | E746_P753 > VS | 19 |
| 2238_2248 > GC | L747_A750 > P | 19 |
| 2238_2252del15 | L747_T751del | 19 |
| 2238_2252 > GCA | L747_T751 > Q | 19 |
| 2238_2255del18 | E746_S752 > D | 19 |
| 2239_2247del9 | L747_E749del | 19 |
| 2239_2248 > C | L747_A750 > P | 19 |
| 2239_2251 > C | L747_T751 > P | 19 |
| 2239_2253del15 | L747_T751del | 19 |
| 2239_2256del18 | L747_S752del | 19 |
| 2239_2256 > CAA | L747_S752 > Q | 19 |
| 2239_2258 > CA | L747_P753 > Q | 19 |
| 2240_2251del12 | L747_T751 > S | 19 |
| 2240_2254del15 | L747_T751del | 19 |
| 2240_2257del18 | L747_P753 > S | 19 |
| 2253_2276del24 | S752_I759del | 19 |

TABLE 1-continued

Examples of EGFR mutations.

| Mutation | Amino Acid Change | Exon |
|---|---|---|
| 2303 G > T | S768I | 20 |
| 2307__2308 ins 9(GCCAGCGTG) | V769__D770insASV | 20 |
| 2309__2310(AC > CCAGCGTGGAT SEQ ID NO: 1) | V769__D770insASV | 20 |
| 2310__2311 ins GGT | D770__N771insG | 20 |
| 2311__2312 ins 9(GCGTGGACA) | D770__N771insSVD | 20 |
| 2319__2320 ins CAC | H773__V774insH | 20 |
| 2369 C > T | T790M | 20 |
| 2573 T > G | L858R | 21 |
| 2573-2574TG > GT | L858R | 21 |

TABLE 2

Summary of the exemplary experimental data used for establishing cut-off limits for a measurable range of quantitative PCR assays.

| | | | Breakthrough Data Ex19 Deletion | | | | |
|---|---|---|---|---|---|---|---|
| Genomic DNA, ng per reaction | # of reactions | Average IC $C_p$ | # of reactions with observed | Average breakthrough $C_p$ | Minimum breakthrough $C_p$ | Average $C_pR$ | Minimum $C_pR$ |
| 500 | 120 | 19.89 | 1 | 40 | 40 | 20.19 | 20.19 |
| 250 | 120 | 20.81 | 3 | 40.42 | 38.79 | 19.65 | 18.16 |
| 125 | 120 | 21.72 | 0 | NA* | NA | NA | NA |
| 62.5 | 120 | 22.67 | 1 | 40.37 | 40.37 | 17.7 | 17.7 |
| 31.3 | 120 | 23.65 | 0 | NA | NA | NA | NA |
| 15.6 | 120 | 24.67 | 0 | NA | NA | NA | NA |
| 7.8 | 119 | 25.74 | 0 | NA | NA | NA | NA |
| 3.9 | 119 | 26.87 | 0 | NA | NA | NA | NA |
| 2 | 119 | 28.05 | 0 | NA | NA | NA | NA |
| 1 | 120 | 29.28 | 0 | NA | NA | NA | NA |
| 0.5 | 107 | 30.50 | 0 | NA | NA | NA | NA |
| 0.25 | 107 | 31.61 | 0 | NA | NA | NA | NA |

| | Breakthrough Data S768I | | | |
|---|---|---|---|---|
| Genomic DNA, ng per reaction | # of reactions with observed | Average breakthrough Cp | Minimum breakthrough Cp | Average $C_pR$ | Minimum $C_pR$ |
| 500 | 4 | 39.01 | 38 | 19.06 | 17.82 |
| 250 | 0 | NA | NA | NA | NA |
| 125 | 1 | 34.01 | 34.01 | 12.27 | 12.27 |
| 62.5 | 1 | 39.02 | 39.02 | 16.18 | 16.18 |
| 31.3 | 2 | 34.53 | 34.19 | 10.84 | 10.56 |
| 15.6 | 0 | NA | NA | NA | NA |
| 7.8 | 2 | 34.36 | 34.29 | 8.44 | 8.41 |
| 3.9 | 0 | NA | NA | NA | NA |
| 2 | 0 | NA | NA | NA | NA |
| 1 | 0 | NA | NA | NA | NA |
| 0.5 | 0 | NA | NA | NA | NA |
| 0.25 | 0 | NA | NA | NA | NA |

*NA stands for "not applicable"

TABLE 3

Summary of Study I experimental data.

| EGFR Activating Mutations | Plasma MUT+* | | Plasma MUT−** | |
|---|---|---|---|---|
| Tissue MUT+ | 13 (metastasis status of 2 samples not known) | | 3 | |
| | pM1a | pM1b*** | pM1a | pM1b |
| | 2 | 9 | 3 | 0 |

*MUT+ = activating mutation detected
**MUT− = activating mutation not detected
***Metastasis status of some of the patients was not known

TABLE 4

Summary of Study I experimental data for the patients with detectable mutations in tissue samples.

| Patient ID | Mutations detected in tissue sample | Mutations detected in plasma sample | Metastasis status |
|---|---|---|---|
| 1 | L858R&T790M | L858R & T790M | N/D* |
| 2 | Ex19Del | Ex19Del | N/D |
| 3 | L858R | L858R | pM1b |
| 4 | S768I, G719X | S768I & G719X | pM1b |
| 5 | L858R | L858R | pM1b |
| 6 | Ex19Del | Ex19Del | pM1a |
| 7 | Ex19Del | Ex19Del & T790M | pM1b |
| 8 | Ex19Del | Ex19Del | pM1b |
| 9 | Ex19Del | Ex19Del | pM1b |
| 10 | Ex19Del | Ex19Del | pM1b |
| 11 | Ex19Del | Ex19Del | pM1b |
| 12 | Ex19Del | Ex19Del | pM1b |
| 13 | L858R | L858R | pM1a |
| 14 | L858R&Ex20Ins | — | pM1a |

TABLE 4-continued

Summary of Study I experimental data for the patients with detectable mutations in tissue samples.

| Patient ID | Mutations detected in tissue sample | Mutations detected in plasma sample | Metastasis status |
|---|---|---|---|
| 15 | L858R and T790M | — | pM1a |
| 16 | Ex19Del & T70M | — | pM1a |

*N/D = not determined

TABLE 5-I

Summary of Study II experimental data

| EGFR Activating Mutations | Plasma MUT+* | | Plasma MUT−** | |
|---|---|---|---|---|
| | pM1a*** | pM1b | pM1a | pM1b |
| Tissue MUT+ | 11 | | 4 | |
| | 1 | 9 | 3 | 1 |

*MUT+ = activating mutation detected
**MUT− = activating mutation not detected
***Metastasis status of some of the patients was not known

TABLE 5-II

Summary of Study II experimental data

| EGFR resistance mutation T790M | Plasma MUT+* | | Plasma MUT−** | |
|---|---|---|---|---|
| | pM1a | pM1b | pM1a | pM1b |
| Tissue MUT+ | 6 | | 3 | |
| | 1 | 5 | 2 | 1 |

*MUT+ = activating mutation detected
**MUT− = activating mutation not detected
***Metastasis status of some of the patients was not known

TABLE 6

Summary of Study II experimental data

| Patient ID | Mutations detected in tissue sample | Mutations detected in plasma sample | Metastasis status |
|---|---|---|---|
| 1 | Ex19Del | Ex19Del | pM1b |
| 2 | L861Q & G719X & T790M | L861Q & G719X & T790M | pM1b |
| 3 | Ex19Del | Ex19Del | pM1b |
| 4 | L858R | L858R | pM1b* |
| 5 | L858R & T790M | L858R & T790M | pM1b |
| 6 | L858R & T790M | L858R & T790M | pM1b |

TABLE 6-continued

Summary of Study II experimental data

| Patient ID | Mutations detected in tissue sample | Mutations detected in plasma sample | Metastasis status |
|---|---|---|---|
| 7 | Ex19Del & T790M | Ex19Del & T790M | pM1b |
| 8 | Ex19Del & T790M | Ex19Del & T790M | pM1b |
| 9 | L858R | L858R | pM1b |
| 10 | Ex19Del & T790M | Ex19Del & T790M | pM1a |
| 11 | Ex19Del & T790M | Ex19Del & T790M | N/D |
| 12 | T790M (Ex19Del) | — | pM1a |
| 13 | Ex19Del & T790M | — | pM1a |
| 14 | Ex19Del & T790M | — | pM1b |
| 15 | Ex19De | — | pM1b |
| 16 | — | Ex19Del | pM1b |
| 17 | — | Ex19Del | pM1b |

*N/D = not determined

TABLE 7

Summary of Study I and Study II data on detection of activating EGFR mutations in blood of NSCLC patients of different metastasis status.

| Study | Metastasis status | Positive agreement | Negative agreement | Overall agreement |
|---|---|---|---|---|
| I | Overall* | 81% | 100% | 89% |
| | pM1a | 40% | | |
| | pM1b | 100% | | |
| II | Overall* | 73% | 0% | 65% |
| | pM1a | 25% | | |
| | pM1b | 90% | | |

*Includes patients with pM1a, pM1b and non-determined metastasis status

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A method of treating a non-small cancer cell lung cancer (NSCLC) patient with a targeted drug therapy, comprising:
   (a) carrying out a PET scan on the NSCLC patient and assessing metastatic status of the NSCLC patient as M1a or M1b;
   (b) based on the assessment in step (a), sorting the NSCLC patient as having metastatic status M1a or M1b;
   (c)(i) obtaining a tumor tissue sample from the NSCLC patient having metastatic status M1a and detecting presence or absence of one or more mutated Epidermal Growth Factor Receptor (EGFR) sequence in the tumor tissue sample from the NSCLC patient by allele-specific PCR;
   (c)(ii) obtaining a blood sample, and not a tumor tissue sample, from the NSCLC patient having metastatic status M1b and detecting presence or absence of one or more mutated Epidermal Growth Factor Receptor (EGFR) sequence in the blood sample from the NSCLC patient by allele-specific PCR; and
   (d) if the presence of an activating EGFR mutation selected from the group consisting of exon 19 deletion, L858R, L861Q, and G719X is detected, administering targeted drug therapy to the NSCLC patient, wherein the targeted drug therapy is an EGFR tyrosine kinase inhibitor.

2. The method of claim 1, wherein the one or more mutated EGFR sequence comprises a resistance EGFR mutation selected from the group consisting of T790M, S678I and an exon 20 insertion.

3. The method of claim 2, wherein the tyrosine kinase inhibitor is an irreversible tyrosine kinase inhibitor.

4. The method of claim 1, wherein the tyrosine kinase inhibitor is erlotinib of gefitinib.

5. The method of claim 1, wherein the presence or absence of one or more mutated EGFR sequence in the blood of the NSCLC patient subject is detected more than one time before, during, or after targeted drug therapy, or any combination thereof.

6. The method of claim 5, increasing the dose of tyrosine kinase inhibitor administered to the NSCLC patient if an increase in quantity of the activating EGFR mutation selected from the group consisting of exon 19 deletion, L858R, L861Q, and G719X is detected.

7. The method of claim 1, further comprising modifying the targeted drug therapy.

8. The method of claim 2, further comprising modifying the targeted drug therapy.

9. The method of claim 5, further comprising modifying the targeted drug therapy.

* * * * *

SEQUENCE LISTING

```
<160> NUMBER OF SEQ ID NOS: 1

<210> SEQ ID NO 1
<211> LENGTH: 11
<212> TYPE: DNA
<213> ORGANISM: Artificial Sequence
<220> FEATURE:
<223> OTHER INFORMATION: synthetic epidermal growth factor receptor
      (EGFR, Her-1, Erb-B1) mutation 2309_2310

<400> SEQUENCE: 1
ccagcgtgga t                                                          11
```